(12) United States Patent
Chae et al.

(10) Patent No.: US 9,999,395 B2
(45) Date of Patent: Jun. 19, 2018

(54) APPARATUS AND METHOD FOR DETECTING USER ACTION

(75) Inventors: Seung-Chul Chae, Seoul (KR);
Sun-Jae Lee, Suwon-si (KR);
Kyung-Ah Chang, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1114 days.

(21) Appl. No.: 13/086,602

(22) Filed: Apr. 14, 2011

(65) Prior Publication Data

US 2012/0032819 A1    Feb. 9, 2012

(30) Foreign Application Priority Data

Aug. 6, 2010    (KR) ........................ 10-2010-0076113

(51) Int. Cl.
*H03K 17/94* (2006.01)
*A61B 5/00* (2006.01)
*A61B 5/11* (2006.01)
*G06F 19/00* (2018.01)

(52) U.S. Cl.
CPC .......... *A61B 5/6898* (2013.01); *A61B 5/1113* (2013.01); *A61B 5/1118* (2013.01); *G06F 19/3418* (2013.01); *A61B 2562/0219* (2013.01)

(58) Field of Classification Search
CPC ...................................................... H03K 17/94
USPC ......................................... 341/20, 21, 22, 23
See application file for complete search history.

(56) References Cited

U.S. PATENT DOCUMENTS

| | | | |
|---|---|---|---|
| 2002/0058517 A1* | 5/2002 | Furukawa | G08B 21/0283 455/456.3 |
| 2006/0161079 A1 | 7/2006 | Choi et al. | |
| 2009/0047998 A1* | 2/2009 | Alberth, Jr. | H04W 52/42 455/562.1 |
| 2009/0286549 A1* | 11/2009 | Canon | G01S 3/74 455/456.1 |
| 2010/0056872 A1* | 3/2010 | Kahn et al. | 600/300 |
| 2010/0095251 A1* | 4/2010 | Dunko | 715/863 |
| 2010/0121716 A1* | 5/2010 | Golan | 705/14.58 |
| 2010/0255856 A1* | 10/2010 | Kansal et al. | 455/456.1 |
| 2011/0312311 A1* | 12/2011 | Abifaker | G06F 3/017 455/418 |

FOREIGN PATENT DOCUMENTS

| | | |
|---|---|---|
| JP | 2004-280376 | 10/2004 |
| JP | 2006-192276 A | 7/2006 |
| JP | 2007-325296 | 12/2007 |
| JP | 2009-39466 A | 2/2009 |

(Continued)

OTHER PUBLICATIONS

Korean Office Action dated Mar. 21, 2017 in corresponding Korean Application No. 10-2010-0076113. (5 pages in Korean with English translation).

*Primary Examiner* — Amine Benlagsir
(74) *Attorney, Agent, or Firm* — NSIP Law (57) ABSTRACT

Provided is an apparatus and method for detecting a user activity using a mobile terminal. The apparatus includes a sensing data collection unit to collect sensing data, a location determination unit to determine a location of the mobile terminal using the sensed data, and an action determination unit to determine an activity of a user that is using the mobile terminal based on the collected sensing data and the determined location of the mobile terminal.

15 Claims, 4 Drawing Sheets

| 301 → | Pocket | | Hands | | Neck | | Floor | |
|---|---|---|---|---|---|---|---|---|
| | REPRESENTATIVE ACTIVITY (302) | DATA PATTERN (303) | REPRESENTATIVE ACTIVITY (302) | DATA PATTERN (303) | REPRESENTATIVE ACTIVITY (302) | DATA PATTERN (303) | REPRESENTATIVE ACTIVITY (302) | DATA PATTERN (303) |
| | Running | Pattern Model #10 | Running | Pattern Model #20 | Running | Pattern Model #30 | Leave alone | Pattern Model #40 |
| | Standing | Pattern Model #11 | Standing | Pattern Model #21 | Standing | Pattern Model #31 | Pick up | Pattern Model #41 |
| | Sitting | Pattern Model #12 | Sitting | Pattern Model #22 | Sitting | Pattern Model #32 | Take a picture | Pattern Model #42 |
| | Ascending Stairs | Pattern Model #13 | Ascending Stairs | Pattern Model #23 | Ascending Stairs | Pattern Model #33 | | |
| | Riding Elevator | Pattern Model #14 | Riding Elevator | Pattern Model #24 | Riding Elevator | Pattern Model #34 | | |
| | Bicycling | Pattern Model #15 | Bicycling | Pattern Model #25 | Bicycling | Pattern Model #35 | | |
| | Descending Stairs | Pattern Model #16 | Descending Stairs | Pattern Model #26 | Descending Stairs | Pattern Model #36 | | |
| | Riding Car | Pattern Model #17 | Riding Car | Pattern Model #27 | Riding Car | Pattern Model #37 | | |
| | | | Take a Picture | Pattern Model #28 | | | | |
| | | | Put down On table | Pattern Model #29 | | | | |

301-1

(56) References Cited

FOREIGN PATENT DOCUMENTS

| KR | 10-2005-0116510 | 12/2005 |
| KR | 10-2006-0083787 | 7/2006 |
| KR | 10-2007-0034849 | 3/2007 |
| KR | 10-2009-0017344 | 2/2009 |

* cited by examiner

| Pocket | | Hands | | Neck | | Floor | |
|---|---|---|---|---|---|---|---|
| REPRESENTATIVE ACTIVITY (302) | DATA PATTERN (303) | REPRESENTATIVE ACTIVITY (302) | DATA PATTERN (303) | REPRESENTATIVE ACTIVITY (302) | DATA PATTERN (303) | REPRESENTATIVE ACTIVITY (302) | DATA PATTERN (303) |
| Running | Pattern Model #10 | Running | Pattern Model #20 | Running | Pattern Model #30 | Leave alone | Pattern Model #40 |
| Standing | Pattern Model #11 | Standing | Pattern Model #21 | Standing | Pattern Model #31 | Pick up | Pattern Model #41 |
| Sitting | Pattern Model #12 | Sitting | Pattern Model #22 | Sitting | Pattern Model #32 | Take a picture | Pattern Model #42 |
| Ascending Stairs | Pattern Model #13 | Ascending Stairs | Pattern Model #23 | Ascending Stairs | Pattern Model #33 | | |
| Riding Elevator | Pattern Model #14 | Riding Elevator | Pattern Model #24 | Riding Elevator | Pattern Model #34 | | |
| Bicycling | Pattern Model #15 | Bicycling | Pattern Model #25 | Bicycling | Pattern Model #35 | | |
| Descending Stairs | Pattern Model #16 | Descending Stairs | Pattern Model #26 | Descending Stairs | Pattern Model #36 | | |
| Riding Car | Pattern Model #17 | Riding Car | Pattern Model #27 | Riding Car | Pattern Model #37 | | |
| | | Take a Picture | Pattern Model #28 | | | | |
| | | Put down On table | Pattern Model #29 | | | | |

APPARATUS AND METHOD FOR DETECTING USER ACTION

CROSS-REFERENCE TO RELATED APPLICATION(S)

This application claims the benefit under 35 U.S.C. § 119(a) of Korean Patent Application No. 10-2010-0076113, filed on Aug. 6, 2010, in the Korean Intellectual Property Office, the entire disclosure of which is incorporated herein by reference for all purposes.

BACKGROUND

1. Field

The following description relates to an apparatus and method for detecting an activity of a user that is using a mobile terminal.

2. Description of the Related Art

Studies on preventive healthcare have been performed to observe the long-term behavior of people in an effort to correct disease-related activity and to warn users of potential risks.

Preventive healthcare may not be based on responding to urgent needs of patients after an attack of a disease, but may be instead used for the prevention of disease-causing habits by informing patients of risky factors through long-term monitoring of the health conditions. Preventive healthcare may be used to correct harmful activities in an effort to prevent the disease itself. In effort to prevent disease, continuous observation and analysis of a patient's activity may be desirable.

The observation and analysis of activities of patients are generally carried out in a hospital or the home of critical patients that receive in-home health aid or who have a dedicated monitoring camera. Recently devices that are attachable to a human body for up to 24 hours or more have been introduced in an effort to monitor and analyze activities of a user without limitation of place and time. However, such devices are typically high in price and are inconvenient for the user to wear at all times.

SUMMARY

In one general aspect, provided is an apparatus for detecting a user activity, the apparatus including a sensing data collection unit configured to collect sensing data from at least one sensor mounted on a mobile terminal, a location determination unit configured to acquire posture data of the mobile terminal based on the collected sensing data, and to determine a location of the mobile terminal based on the acquired posture data and a location model comprising location candidates of the mobile terminal which correspond to the posture data, and an action determination unit configured to determine an activity of a user based on the determined location of the mobile terminal, the collected sensing data, and an activity model comprising activity candidates of the user which correspond to the locations and the sensing data.

The location determination unit may be further configured to acquire the posture data using sensing data of a triaxial acceleration sensor.

The posture data may comprise information about inclinations with respect to the respective axes of a coordinate system for the triaxial acceleration sensor.

The location determination unit may be further configured to select at least one location candidate from the location model based on the acquired posture data, and select a final location from the selected location candidates based on the collected sensing data.

The location determination unit may be further configured to select the location candidates by comparing the acquired posture data and modeled posture data of the location model, and select the final location from the location candidates based on at least one of sensing data from the triaxial acceleration sensor, a proximity sensor, an orientation sensor, a terrestrial magnetism sensor, a display ON/OFF monitoring sensor, and a sound detection sensor.

The action determination unit may be further configured to select at least one activity candidate from the activity model based on the determined location of the mobile terminal, and select a final activity from the selected activity candidates based on the collected sensing data.

The location model may further comprise probability increase conditions with respect to the respective locations of the mobile terminal.

In another aspect, there is provided a method of detecting a user activity, the method comprising collecting sensing data from at least one sensor mounted on a mobile terminal, acquiring posture data of the mobile terminal based on the collected sensing data, and determining a location of the mobile terminal based on the acquired posture data and a location model comprising location candidates of the mobile terminal which correspond to the posture data, and determining an activity of the user based on the determined location of the mobile terminal, the collected sensing data, and an activity model comprising activity candidates of the user which correspond to the locations and the sensing data.

The determining of the location may comprise acquiring the posture data using sensing data of a triaxial acceleration sensor.

The determining of the location may comprise selecting at least one location candidate from the location model based on the acquired posture data, and selecting a final location from the selected location candidates based on the collected sensing data.

The determining of the location may comprise selecting the location candidates by comparing the acquired posture data and modeled posture data of the location model, and selecting the final location from the location candidates based on at least one of sensing data from the triaxial acceleration sensor, a proximity sensor, an orientation sensor, a terrestrial magnetism sensor, a display ON/OFF monitoring sensor, and a sound detection sensor.

The determining of the activity may comprise selecting at least one activity candidate from the activity model based on the determined location of the mobile terminal and selecting a final activity from the selected activity candidates based on the collected sensing data.

In another aspect, there is provided a mobile terminal for detecting a user activity, the apparatus comprising a sensing data collection unit configured to collect sensing data, a location determination unit configured to determine an orientation and a movement of the mobile terminal based on the collected sensing data, and to determine a location of the mobile terminal based on the determined orientation and movement, and an action determination unit configured to determine an activity of a user of the mobile terminal based on the determined location of the mobile terminal.

The location determination unit may determine the location of the mobile terminal based on a location model that comprises possible locations of the mobile terminal, orientation and movement information which the mobile terminal is likely to have at the possible locations, and elements that increase the probability of the presence of the mobile terminal at the possible locations.

The sensing data collection unit may comprise a triaxial acceleration sensor to obtain orientation and movement information about the mobile terminal, and the location determination unit may determine the location of the mobile terminal based on data sensed by the triaxial acceleration sensor.

The action determination unit may determine the activity of the user based on an activity model that comprises possible actions of the mobile terminal, orientation and movement information which the mobile terminal is likely to have during the possible actions, and data patterns corresponding to the possible actions.

Other features and aspects will be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein may be suggested to those of ordinary skill in the art. Also, descriptions of well-known functions and constructions may be omitted for increased clarity and conciseness.

Figure 1:
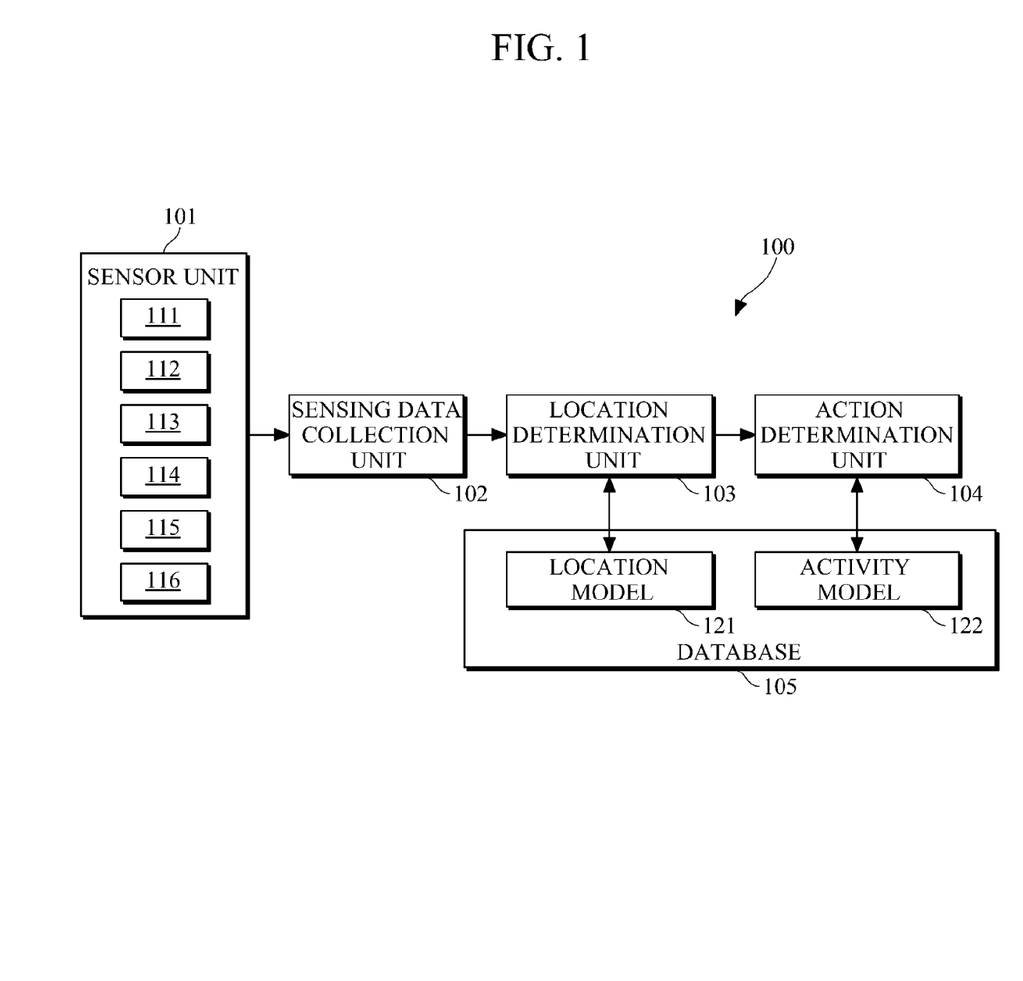
FIG. 1 is a diagram illustrating an example of an apparatus for detecting an activity of a user.

FIG. 1 illustrates an example of an apparatus for detecting an action of a user.

Referring to the example illustrated in FIG. 1, apparatus 100 may correspond to or may be included in a mobile terminal that is designed to be used while being transported by a user. Examples of the mobile terminal may include a mobile phone, a smart phone, a personal digital assistant (PDA), a portable multimedia player (PMP), an MP3 player, and the like.

The apparatus 100 may monitor a status of an action of the user, for example, standing, sitting, or running. The monitoring may be based on a variety of sensing information. In the example illustrated in FIG. 1, the apparatus 100 includes a sensor unit 101, a sensing data collection unit 102, a location determination unit 103, an action determination unit 104, and a database 105.

The sensor unit 101 may sense a variety of information related to the mobile terminal or the user of the mobile terminal. For example, the sensor unit 101 may include a triaxial acceleration sensor 111 that may measure a moving direction and/or a speed of the mobile terminal, a proximity sensor 112 that may measure the presence of an object approaching the mobile terminal, an orientation sensor 113, a terrestrial magnetism sensor 114, a sensor 115 for sensing an ON/OFF status of a display of the mobile terminal, a sound detection sensor 116, and the like. It should be appreciated that the sensor unit 101 is not limited to these types of sensors, for example, the sensor unit 101 may include a gravimeter sensor, an angular velocity sensor, an illuminance sensor, a global positioning system (GPS) sensor, and the like.

The sensing data collection unit 102 may collect sensing data of the sensor unit 101. For example, when a user of the mobile terminal makes a specific gesture, sensing data of the sensor unit 101 may be changed, and the sensing data collection unit 102 may collect the sensing data. The sensing data of the user may vary with time on a sensor module-by-sensor module basis, wherein the sensor modules are included in the sensor unit 101.

The location determination unit 103 may determine where the mobile terminal is located. For example, the location determination unit 103 may specify a location of the mobile terminal. For example, the determined location may indicate a location from among various locations in a user's body or surrounding space, in which the mobile terminal is likely present at.

The location determination unit 103 may determine the location of the mobile terminal using the sensing data collected by the sensing data collection unit 102 and a predetermined location model 121 stored in the database 105. For example, the location model 121 may define locations at which the mobile terminal may possibly be present at, posture patterns which the mobile terminal is likely to take at the respective locations, and elements that increase the probability of the presence of the mobile terminal at the respective locations. As another example, the location determination unit 103 may include location candidates of the mobile terminal which correspond to the posture data.

As described herein, posture may refer to a disposition of the mobile terminal, for example, the orientation at which the mobile terminal is disposed in the X, Y, and Z axes. The posture may refer to the movement of the mobile terminal. For example, one location of the mobile terminal may be in the "Pocket," and the posture patterns included in the location model 121 may include a typical orientation of the mobile terminal or an estimated orientation of the mobile terminal in the X, Y, and Z axes when the mobile terminal is located in the "Pocket." As another example, the posture patterns may include an estimated or typical movement of the mobile terminal when the mobile terminal is located in the "Pocket."

For example, the location determination unit 103 may infer the posture of the mobile terminal using sensing data. In response to inferring the orientation of the mobile terminal, the location determination unit 103 may extract a number of location candidates by comparing the inferred posture of the mobile terminal with the posture patterns for the respective locations in the location model 121. In response to the extraction of the location candidates, the location determination unit 103 may deduce elements that increase the probability of the presence of the mobile terminal at each location using the sensing data, and may determine a final location from the location candidates based on the result of the deduction.

The action determination unit 104 may determine an action of the user of the mobile terminal. For example, the action determination unit 104 may determine an action of the user. The determination of action may indicate selection of an action from various actions that the user can take.

For example, the action determination unit 104 may determine the action of the user using the sensing data collected by the sensing data collection unit 102, the location of the mobile terminal determined by the location determination unit 103, and/or a predefined action model 122 stored in the database 105. For example, the action model 122 may define possible actions the mobile terminal may take, posture patterns which the user of the mobile terminal is likely to take have during the possible actions, and data patterns corresponding to the respective actions. As another example, the action model 122 may include activity candidates of the user which correspond to the locations and the sensing data.

For example, the action determination unit 104 may extract a number of action candidates that correspond to the respective locations determined by the location determination unit 103 from the action model 122. In response to the extraction of the location candidates, the action determination unit 104 may select a final action that has the highest probability from the action candidates by comparing the data pattern of the sensing data corresponding to the extracted action candidates with the sensing data collected by the sensing data collection unit 102.

The database 105 may store the location model 121 and the action model 122. As an example, the location model 121 and the action model 122 stored in the database 105 may be generated by machine learning and/or updated according to user settings such as rules.

The mobile terminal may generally be carried by a user at all times. Thus, the apparatus 100 which infers an action of the user using various sensing data of the mobile terminal may monitor the actions of the user continuously using the mobile terminal without an additional dedicated device. For example, because an action may be determined through the action model 122 after the location of the mobile terminal has been confirmed by means of the location model 121, various actions that the user can take at the confirmed location of the mobile terminal may be restricted, and thus, the user action may be promptly inferred.

The data collected by the sensing data collection unit 102 may include noises, for example, noises that are caused by the continuous changes in the position of the mobile terminal and noises that are caused by the use status of the mobile terminal. As an example, noises may be eliminated or reduced by a Karman filter before the comparison with the location model 121 and the action model 122 occurs.

Figure 2:
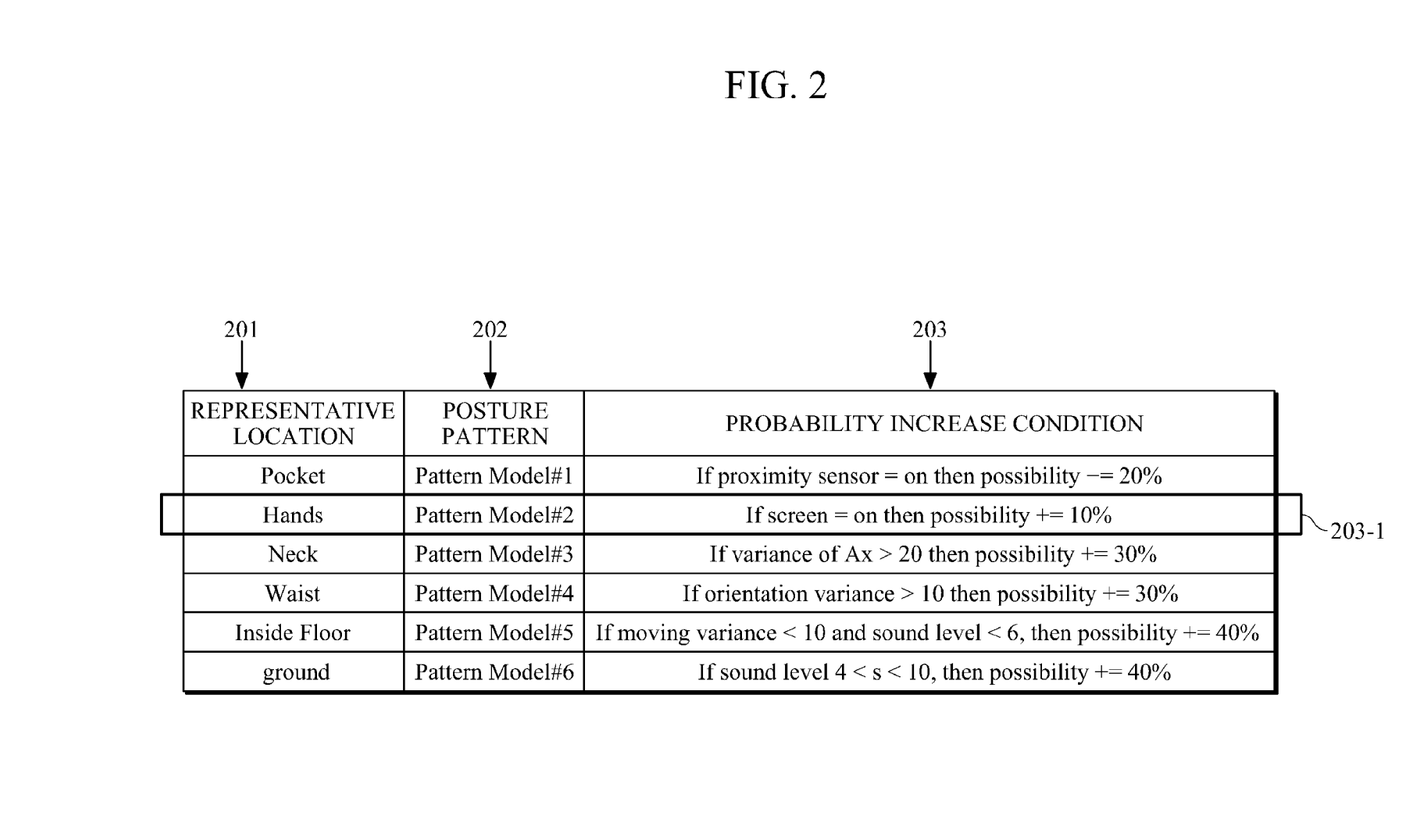
FIG. 2 is a diagram illustrating an example of a location model.

FIG. 2 illustrates an example of a location model.

Referring to the example illustrated in FIG. 2, the location model may include a plurality of elements, for example, three modeling elements. A first element may be a modeling element about a location at which a mobile terminal is likely to be present at. In the example illustrated in FIG. 2, the first element is referred to as a representative location 201. A second element is a modeling element about a posture of the mobile terminal at each representative location 201. In the example illustrated in FIG. 2, the second element is referred to as a posture pattern 202. A third element is a modeling element about a condition that increases the probability of the presence of the mobile terminal at each representative location 201. In the example illustrated in FIG. 2, the third element is referred to as a probability increase condition 203.

As shown in the examples illustrated in FIGS. 1 and 2, the location determination unit 103 may determine the location of the mobile terminal based on the posture information of the mobile terminal which may be obtained from the sensing data and the posture pattern 202 and the probability increase condition 203 of the location model 121.

For example, the location determination unit 103 may use sensor values of the triaxial acceleration sensor 111 to obtain the posture location of the mobile terminal as shown in Equations (1) below.

$$\text{pitch} = \arctan(Ax/\sqrt{Ay^2 + Az^2})$$

$$\text{roll} = \arctan(Ay/\sqrt{Ax^2 + Az^2})$$

$$\text{theta} = \arctan(\sqrt{Ax^2 + Az^2}/Az) \quad (1)$$

In Equation 1, Ax, Ay, and Az indicate sensor values of the triaxial acceleration sensor 111. In this example, pitch, roll, and theta indicate inclinations with respect to the respective axes of a coordinate system of the triaxial acceleration sensor 111. For example, the posture information of the mobile terminal may be represented as (pitch, roll, theta).

In response to the acquisition of the posture information of the mobile terminal, the location determination unit 103 may select at least one representative location 201 as a location candidate by comparing the acquired posture information and the posture pattern 202 of the location model 121. For example, if the acquired posture information is similar to pattern model #1 and pattern model #2 from among the posture patterns 202, the location determination unit 103 may select "Pocket" and "Hands" as location candidates.

In response to the selection of the location candidates, the location determination unit 103 may analyze whether data that satisfies the probability increase condition 203 is present among the sensing data collected by the sensing data collection unit 102. For example, if sensing data of the sensor 115 for monitoring an ON/OFF status of a display of the mobile terminal is received, the mobile terminal may be more likely to be in the hands not in the pocket. As a result, the location determination unit 103 may select "Hands" as a final location with reference to the probability increase condition 203-1.

In certain aspects, the location determination unit 103 may determine a location of the mobile terminal based on the posture information obtained from the sensing data and the location model. For example, if the mobile terminal is in a standing erect position and the proximity sensor 110 is in an ON state, the mobile terminal may be assumed to be in the pocket, and if the proximity sensor 110 is in an OFF state, the mobile terminal may be assumed to be in the hands.

Figure 3:
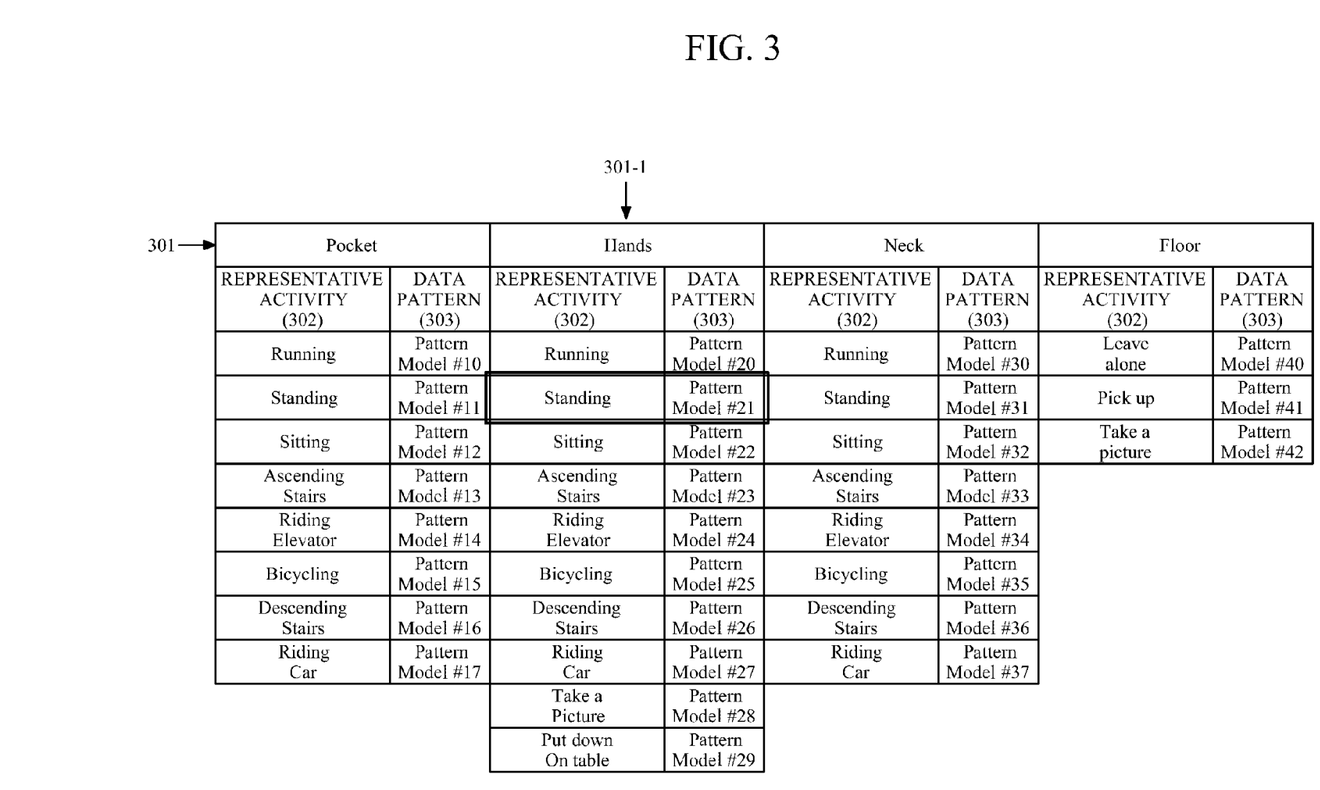
FIG. 3 is a diagram illustrating an example of an activity model.

FIG. 3 illustrates an example of an activity model.

Referring to the example illustrated in FIG. 3, the activity model may include three types of modeling elements. For example, a first element may be related to locations at which the mobile terminal is likely to be present at. In the example illustrated in FIG. 3, the first element represents a location 301. A second element corresponds to activities that a user of the mobile terminal may take at the respective locations 301. In the example illustrated in FIG. 3, the second element is referred to as a representative activity 302. A third element may be modeling data about sensing data in which the user takes the respective representative activities. For example, the third element may be pattern data that is obtained by pattern sensing data collected based on the activity that the user takes. In the example illustrated in FIG. 3, the third element is referred to as a data pattern 303.

In regard to the representative activity 302, as an example, if the location of the mobile terminal is decided, the activities that the user may possibly take at the decided location may be limited.

Referring to the examples illustrated in FIGS. 1 to 3, the activity determination unit 104 may select one from the representative locations 301 of the activity model 122 based on the location of the mobile terminal which is determined by the location determination unit 103. For example, as shown in FIG. 2, if it is determined that the mobile terminal is in the hands, the activity determination unit 104 may select a location 301-1 that corresponds to the hands from among the representative locations 301. The activity determination unit 104 may select the representative activity 302 corresponding to the selected representative location 301-1 as a location candidate.

In response to the selection of location candidates, the activity determination unit 104 may select a final activity by comparing the sensing data collected by the sensing data collection unit 102 and the data patterns 303 corresponding to the respective activities 302 selected as the activity candidates. For example, if the collected sensing data is similar to pattern model #21 of the data patterns 303, "Standing" may be selected as the final activity.

Because the activity determination unit 104 may search for the activities possible at a current location after the current location of the mobile terminal has been decided, the user activities may be determined accurately and fast.

Figure 4:
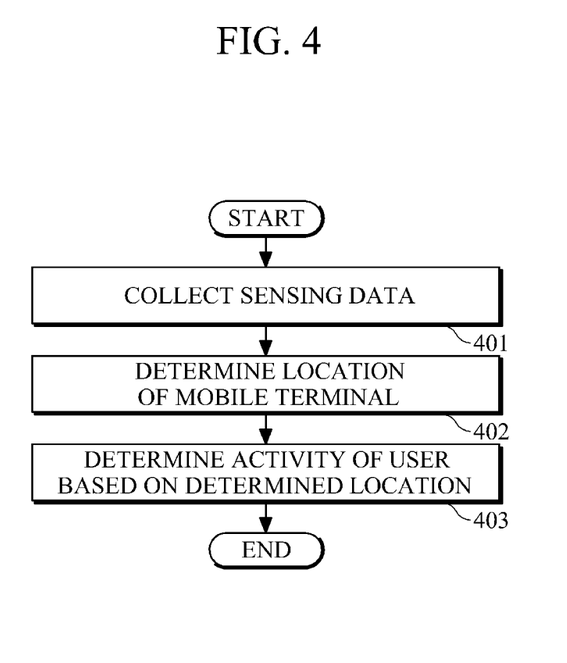
FIG. 4 is a flowchart illustrating an example of a method of detecting a user's activity.

FIG. 4 illustrates an example of a method of detecting a user's activity.

Referring to the example illustrated in FIG. 4, sensing data is collected, in 401. For example, the sensing data collection unit 102 may collect sensor values from the triaxial acceleration sensor 111, the proximity sensor 112, the orientation sensor 113, the terrestrial magnetism sensor 114, the sensor 115 for sensing an ON/OFF status of a display of the mobile terminal, and the sound detection sensor 116 shown in FIG. 1.

In 402, the location of the mobile terminal is determined. For example, the location determination unit 103 may select at least one location candidate from the location model based on posture information obtained from the collected sensing data, and may select a final location from the location candidates based on the collected sensing data.

In 402, an activity of the user is determined based on the determined location. For example, in the examples illustrated in FIGS. 1 and 3, the activity determination unit 104 may select at least one activity candidate from the activity model 122 based on the determined location of the mobile terminal, and may select a final activity from the selected activity candidates based on the collected sensing data.

In various aspects, provided is an apparatus and method for detecting a user activity. For example, the apparatus may be a mobile terminal for detecting a user activity. The apparatus may comprise a sensing data collection unit configured to collect sensing data. The sensing data collection unit may include various sensors to determine the position and movement of the apparatus, for example, a triaxial acceleration sensor.

The apparatus may include a location determination unit configured to determine an orientation and a movement of the mobile terminal based on the collected sensing data, and to determine a location of the mobile terminal based on the determined orientation and movement. For example, the location determination unit may determine the location of the mobile terminal based on a location model that comprises possible locations of the mobile terminal, orientation and movement information which the mobile terminal is likely to have at the possible locations, and elements that increase the probability of the presence of the mobile terminal at the possible locations.

The apparatus may include an action determination unit configured to determine an activity of a user of the apparatus based on the determined location of the mobile terminal and an activity model comprising possible activities of the user. For example, the activity model may comprise possible actions of the mobile terminal, orientation and movement information which the mobile terminal is likely to have during the possible actions, and data patterns corresponding to the possible actions.

The methods, processes, functions, and software described herein may be recorded, stored, or fixed in one or more computer-readable storage media that includes program instructions to be implemented by a computer to cause a processor to execute or perform the program instructions. The media may also include, alone or in combination with the program instructions, data files, data structures, and the like. The media and program instructions may be those specially designed and constructed, or they may be of the kind well-known and available to those having skill in the computer software arts. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for detecting a user activity, the apparatus comprising:
a sensing data collector configured to collect sensing data from a sensor mounted on a mobile terminal of a user;
a location determiner configured to acquire posture data of the mobile terminal based on the collected sensing data, and to determine a location of the mobile terminal relative to the user based on the acquired posture data and location probabilities comprising probability increase conditions, wherein the probability increase condition is a modeling element about a condition that increases a probability of a presence of the mobile terminal at a representative location, with respect to possible locations of the mobile terminal relative to the user; and
an action determiner configured to determine the activity of the user based on the determined location of the mobile terminal relative to the user, the collected sensing data, and representative activities, wherein the action determiner is further configured to select the activity of the user, from among the representative activities, based upon the determined location of the mobile terminal relative to the user and a data pattern with a highest probability of matching the collected sensing data, and wherein the location determiner is further configured to select location candidates based on the acquired posture data and the location probabilities, and select the determined location of the mobile terminal relative to the user from the location candidates based on the collected sensing data from any combination of any two or more of a triaxial acceleration sensor, a proximity sensor, an orientation sensor, a terrestrial magnetism sensor, a display ON/OFF monitoring sensor, and a sound detection sensor.

2. The apparatus of claim 1, wherein the location determiner is further configured to acquire the posture data using the collected sensing data of the triaxial acceleration sensor.

3. The apparatus of claim 2, wherein the acquired posture data comprises information about inclinations with respect to respective axes of a coordinate system for the triaxial acceleration sensor.

4. The apparatus of claim 1, wherein the action determiner is further configured to determine the activity of the user by restricting the representative activities based on the determined location of the mobile terminal relative to the user.

5. The apparatus of claim 1, wherein the acquiring of the posture data is based on a posture pattern, and the location of the mobile terminal relative to the user is based on a probability that the posture pattern indicates that the mobile terminal is located at a particular location relative to the user.

6. The apparatus of claim 5, wherein the location of the mobile terminal relative to the user is one of a pocket of the user, hands of the user, a neck of the user, and a waist of the user.

7. The apparatus of claim 1, wherein the location of the mobile terminal relative to the user is a portion, of a body of the user, to which the mobile terminal is most probable to be proximate.

8. A method of detecting a user activity, the method comprising:

collecting sensing data from a sensor mounted on a mobile terminal of a user;

acquiring posture data of the mobile terminal based on the collected sensing data, and determining a location of the mobile terminal relative to the user based on the acquired posture data and location probabilities comprising probability increase conditions, wherein the probability increase condition is a modeling element about a condition that increases a probability of a presence of the mobile terminal at a representative location, with respect to possible locations of the mobile terminal relative to the user; and determining an activity of the user based on the determined location of the mobile terminal relative to the user, the collected sensing data, and representative activities, wherein the determining of the activity of the user further comprises selecting the activity of the user, from among the representative activities, based upon the determined location of the mobile terminal relative to the user and a data pattern with a highest probability of matching the collected sensing data, and wherein the determining of the location of the mobile terminal relative to the user further comprises selecting location candidates by comparing the acquired posture data and the location probabilities, and selecting the determined location of the mobile terminal relative to the user from the selected location candidates based on the collected sensing data from any combination of any two or more of a triaxial acceleration sensor, a proximity sensor, an orientation sensor, a terrestrial magnetism sensor, a display ON/OFF monitoring sensor, and a sound detection sensor.

9. The method of claim 8, wherein the acquiring of the posture data of the mobile terminal based on the collected sensing data comprises using the collected sensing data of the triaxial acceleration sensor.

10. The method of claim 8, wherein the data pattern is chosen from a plurality of data patterns comprising a data pattern associated with each representative activity, and wherein the selecting of the activity of the user further comprises determining the probability of said each representative activity's associated data pattern matching the collected sensing data.

11. The method of claim 8, wherein the location of the mobile terminal relative to the user is a portion, of a body of the user, to which the mobile terminal is most probable to be proximate.

12. A mobile terminal for detecting a user activity, the mobile terminal comprising:

a sensing data collector configured to collect sensing data from a sensor mounted on the mobile terminal of a user;

a location determiner configured to determine an orientation and a movement of the mobile terminal based on the collected sensing data, and to determine a location of the mobile terminal relative to the user based on the orientation and the movement and location probabilities comprising probability increase conditions, wherein the probability increase condition is a modeling element about a condition that increases a probability of a presence of the mobile terminal at a representative location, with respect to possible locations of the mobile terminal relative to the user; and an action determiner configured to determine the activity of the user based on the determined location of the mobile terminal relative to the user, the collected sensing data, and representative activities, wherein the action determiner is further configured to determine the activity of the user based further on the representative activities, based upon the determined location of the mobile terminal relative to the user and a data pattern with a highest probability of matching the orientation and the movement of the mobile terminal, and wherein the location determiner is further configured to select location candidates based on the orientation and the movement of the mobile terminal and the location probabilities, and select the determined location of the mobile terminal relative to the user from the location candidates based on the collected sensing data from any combination of any two or more of a triaxial acceleration sensor, a proximity sensor, an orientation sensor, a terrestrial magnetism sensor, a display ON/OFF monitoring sensor, and a sound detection sensor.

13. The mobile terminal of claim 12, wherein the location determiner is further configured to determine the location of the mobile terminal relative to the user based on possible detected locations of the mobile terminal, orientations and movements that the mobile terminal is likely to have at the possible detected locations, and the location probabilities.

14. The mobile terminal of claim 12, wherein the sensing data collector comprises the triaxial acceleration sensor configured to obtain the orientation and the movement of the mobile terminal, and the location determiner is further configured to determine the location of the mobile terminal based on data sensed by the triaxial acceleration sensor.

15. The apparatus of claim 12, wherein the location of the mobile terminal relative to the user is a portion, of a body of the user, to which the mobile terminal is most probable to be proximate.

* * * * *